United States Patent [19]

Batty, Jr.

[11] Patent Number: 4,532,932
[45] Date of Patent: Aug. 6, 1985

[54] IMPLANT COMMUNICATION SYSTEM WITH FREQUENCY SHIFT MEANS

[75] Inventor: John R. Batty, Jr., Miami, Fla.
[73] Assignee: Cordis Corporation, Miami, Fla.
[21] Appl. No.: 567,933
[22] Filed: Jan. 3, 1984
[51] Int. Cl.$^3$ ............................................. A61N 1/08
[52] U.S. Cl. .............................. 128/631; 128/419 PT; 340/870.31
[58] Field of Search ................... 128/419 PT, 419 PG, 128/631, 903; 340/870.1, 870.31

[56] References Cited

U.S. PATENT DOCUMENTS

| | | | |
|---|---|---|---|
| 2,823,862 | 2/1958 | Moore, Jr. .................. | 340/870.31 |
| 3,255,588 | 5/1966 | Vuilleumier et al. ......... | 128/631 |
| 4,223,679 | 9/1980 | Schulman et al. ............ | 128/419 PT |
| 4,281,664 | 8/1981 | Duggan ..................... | 128/419 PT |
| 4,361,153 | 11/1982 | Slocum et al. . | |
| 4,416,283 | 11/1983 | Slocum ..................... | 128/419 PG |

Primary Examiner—William E. Kamm
Assistant Examiner—Mitchell J. Shein
Attorney, Agent, or Firm—George H. Gerstman

[57] ABSTRACT

An implant communication system is disclosed for use with an enclosure having a tuned coil mounted therein that is implanted in a patient. A low impedance shunt circuit is connected across the tuned coil, with the impedance of the shunt circuit being modulated in accordance with a data signal. The tuned coil reradiates the phase and amplitude of an externally generated magnetic carrier signal at a selected frequency. A second shunt circuit is connected across the tuned coil for changing its tuning, to enable the tuned frequency to correspond to the selected frequency.

7 Claims, 3 Drawing Figures 4,532,932

IMPLANT COMMUNICATION SYSTEM WITH FREQUENCY SHIFT MEANS

BACKGROUND OF THE INVENTION

The present invention concerns a novel apparatus and process for enabling selected tuning of the tuned coil in an enclosure that is implanted in a patient.

In U.S. Pat. No. 4,361,153, issued Nov. 30, 1982 and assigned to the assignee of the present invention, there is disclosed the use of a resonant impedance modulated transponder, in a device implanted in the patient, to modulate the phase of a reflected magnetic signal that is the product of a magnetic carrier imposed from outside of the body. In this manner, information is transmitted from a fixed internal implant to a positionable external telemetry unit. A relative high energy magnetic field at a carrier frequency is established by a transmitter in the external unit. The field permeates the skin, underlying tissue and case of the implant and induces a signal in a resonant, impedance modulated transponder in the implant tuned to the carrier frequency. A second field is reradiated or reflected at the carrier frequency by the resonant transponder. The transponder's impedance is varied in accordance with a modulation input signal, causing a shift in the phase angle and amplitude of the transponder's contribution to the composite reflected signal, thereby resulting in a proportional phase and amplitude shift in the composite reflected signal. The composite reflected signal is picked up and demodulated by a phase shift detector in the external telemetry unit.

While certain telemetry units generate a carrier signal at a first frequency, for example 16 kilohertz, other telemetry units may generate a carrier signal at a different frequency, for example, 64 kilohertz. Since the higher frequency allows more sampling of the data per second, it is sometimes found desirable to use the higher frequency carrier signal.

If the resonant frequency of the transponder in the implant is tuned to a lower frequency, for example, 16 kilohertz and a higher frequency carrier signal, for example, 64 kilohertz, is utilized, the detected phase and amplitude shift in the composite reflected signal is relatively poor.

It is, therefore, an object of the present invention to provide a system for enabling the changing of the tuned frequency, so that it can correspond to the selected carrier frequency generated by the external unit.

It is also an object of the present invention to provide a system for selectively tuning a tank circuit that is efficient to manufacture and reliable in use.

Further objects and advantages of the present invention will become apparent as the description proceeds.

BRIEF DESCRIPTION OF THE INVENTION

In accordance with the present invention, an implant communication system is provided which includes an enclosure to be implanted. A coiled tuned to a first frequency is mounted within the enclosure. A low impedance shunt circuit is connected across the tuned coil, with the circuit including a device for modulating the impedance of the shunt circuit in accordance with a data signal. In this manner, there is alteration of the phase and amplitude of a signal that is reradiated by the tuned coil in the presence of an externally generated magnetic carrier signal at a selected frequency.

A second shunt circuit is connected across the tuned coil and includes means for changing the tuning of the tuned coil to enable the tuned frequency to correspond to the selected frequency.

In the illustrative embodiment, the second shunt circuit comprises a capacitor and a switch. Means are provided for operating the switch.

In the illustrative embodiment, the second shunt circuit comprises a pair of capacitors and a pair of FETs. Each of the FETs has its source connected to ground, its drain connected to one of the capacitors and its gate connected to the gate of the other FET. Means are coupled to the gates for switching the state of both FETs.

A more detailed explanation of the invention is provided in the following description and claims, and is illustrated in the accompanying drawings.

DETAILED DESCRIPTION OF THE ILLUSTRATIVE EMBODIMENT

Figure 1:
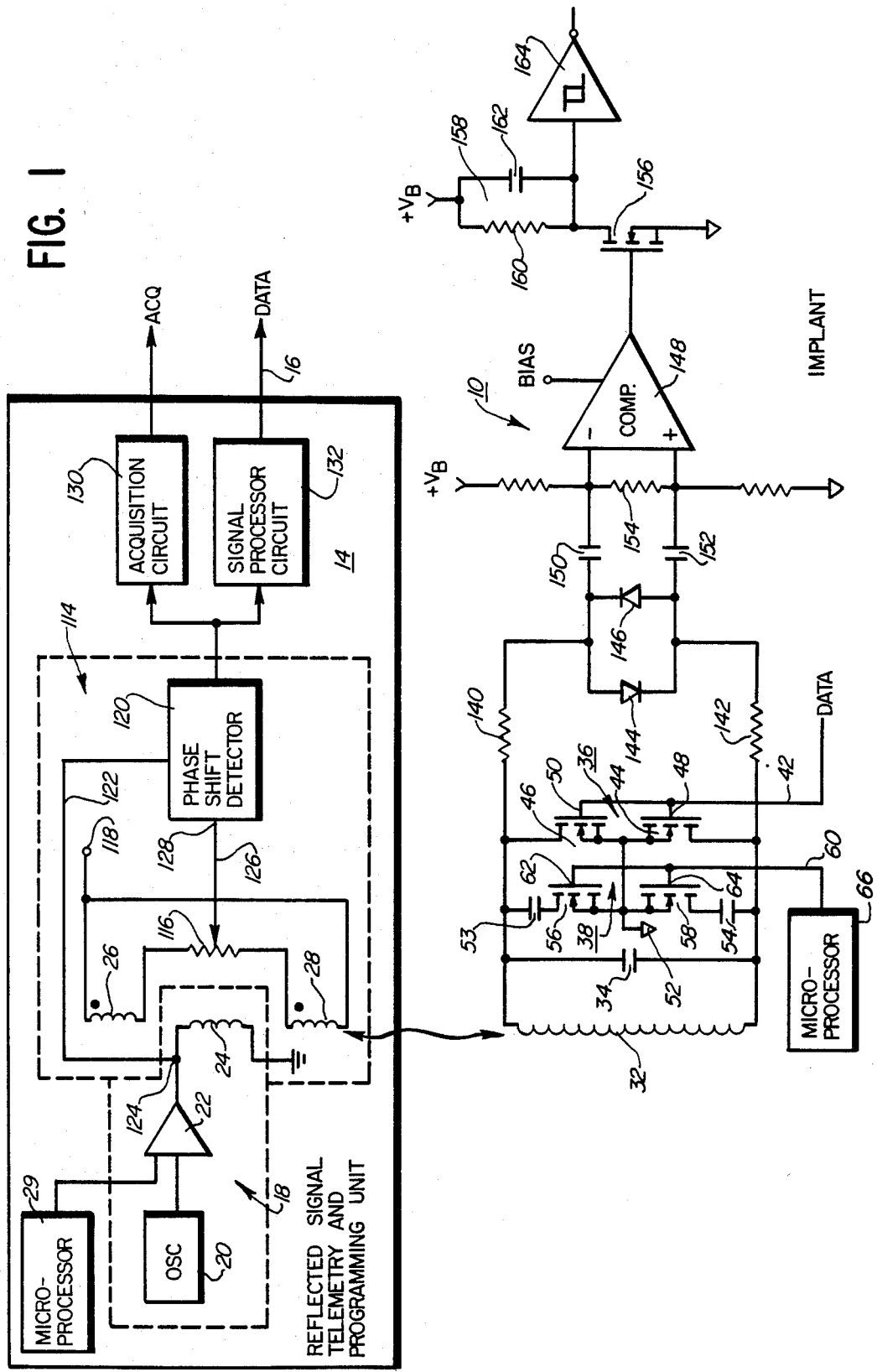
FIG. 1 is a block diagram of an implant communication system, constructed in accordance with the principals of the present invention.

Referring to FIG. 1, an enclosure including the implant circuit 10 (illustrated in the bottom half of FIG. 1) is implanted within a patient's body. An external reflected signal telemetry and programming unit 14 is illustrated for receiving the reflected signal and providing an output representing the data via line 16.

The external reflected signal telemetry and programming unit 14 includes a carrier transmitter 18 having an oscillator 20 which generates a carrier wave at a selected frequency. The oscillator output is fed via a driver amplifier 22 to the middle coil 24 in a triple coil assembly comprising coils 24, 26 and 28.

In telemetry operation, driver amplifier 22 is instructed by microprocessor 29 to enable a continuous wave to be outputted from driver amplifier 22. On the other hand, in its programming mode microprocessor 29 instructs driver amplifier 22 to provide appropriate data pulses at its output.

In the implant 10, a reflected signal transponder includes a coil 32, the ends of which are connected in parallel with a capacitor 34 and a variable impedance means 36 which forms the load into which the tuned coil (coil 32 and capacitor 34) is terminated electrically. The resonant or band pass frequency of the tuned coil is preferably centered at the carrier frequency of the waveform produced by oscillator 20.

However, in the event that a different carrier frequency is utilized, a second shunt circuit 38 is connected across the tuned coil in order to enable the resonant or band pass frequency of the tuned coil to be centered at the carrier frequency.

The oscillating current through the coil 24 in the telemetry unit establishes a magnetic field which radiates into the adjacent implant and induces a corresponding voltage in tuned coil 32 which in turn reradiates a secondary magnetic field at the same carrier frequency. However, when conducting, variable impedance means 36 act as a low resistance shunt across the tuned coil which removes the capacitive reactance of the transponder and alters the phase of the reflected signal.

The input to variable impedance means 36 is the data signal which is fed via line 42 to variable impedance means 36.

In the FIG. 1 embodiment, variable impedance means 36 comprises a matched pair of FETs 44 and 46 with input line 42 connected directly to common gates 48 and 50, with the drains of the FETs connected to the tuned coil and the sources connected to ground 52. In the illustrative embodiment, FETs 44 and 46 comprise N-type MOS FETs.

Second shunt circuit 38 includes a capacitor 53, a capacitor 54, and a matched pair of FETs 56, 58 with input line 60 connected directly to common gates 62 and 64, with the drain of FET 56 connected to capacitor 53, the drain of FET 58 connected directly to capacitor 54, and the sources of both FETs 56 and 58 being connected to ground 52. In the illustrative embodiment, FETs 56 and 58 comprises N-type MOS FETs.

The state of FETs 56 and 58 is controlled by the signal on line 60 which is provided by microprocessor 66. Capacitors 53 and 54 are selected so that when FETs 56 and 58 are conducting, capacitors 52 and 54 will operate in conjunction with capacitors 34 to tune the coil 32 to a selected frequency. For example, with FETs 56 and 58 in their non-conducting state, coil 32 may be tuned to 64 kilohertz. On the other hand, with an appropriate signal from microprocessor 66 on line 60, and the FETs in their conducting state, coil 32 may be tuned to 16 kilohertz.

Figure 2:
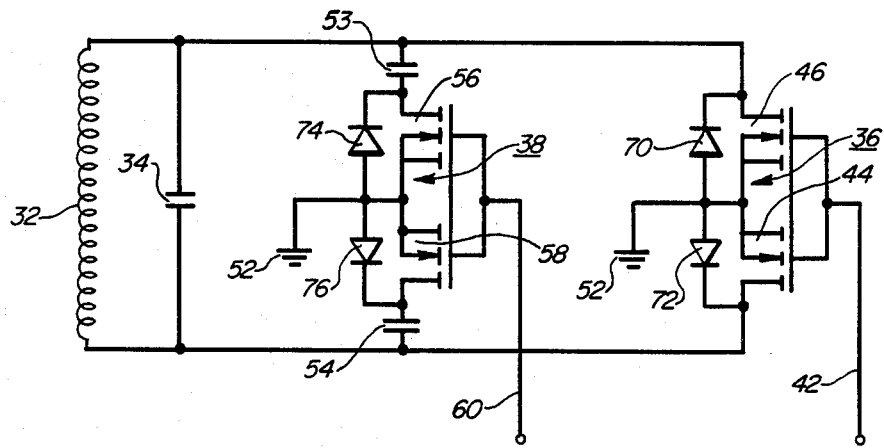
FIG. 2 is a schematic circuit diagram of one form of the tank circuit of the system of FIG. 1.

FETs 46, 48, 56 and 58 are preferably N-type DMOS FETs. As a part of the fabrication procedure, there is inherently a "parasitic diode" across each DMOS FET, as illustrated in FIG. 2. Referring to FIG. 2, it can be seen that parasitic diode 70 is across the source-drain circuit of FET 46; parasitic diode 72 is across the source-drain circuit of FET 48; parasitic diode 74 is across the source-drain circuit of FET 56; and parasitic diode 76 is across the source-drain circuit of FET 58. Diodes 70, 72 and diodes 74, 76 are series-opposing. FETs 46, 48 have common gates and FETs 56, 58 have common gates. In this manner, each pair conducts together, preventing a series path created across the diodes. Hence, one of the diodes will be blocking while the other diode is conducting.

Figure 3:
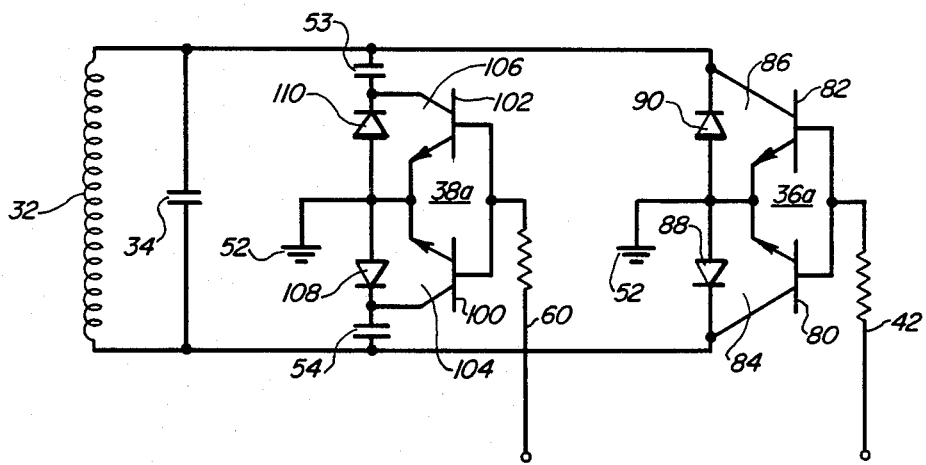
FIG. 3 is a schematic circuit diagram of another form of the tank circuit of the system of FIG. 1.

In a modified form of the invention, another type of variable impedance means 36a and another type of shunt circuit 38a is illustrated. The same reference numerals are used in FIG. 3 for items which are identical to the items of FIGS. 1 and 2. In the FIG. 3 embodiment, line 42 is connected to common bases 80 and 82 of NPN transistors 84 and 86, respectively. A diode 88 is connected across the emitter-collector circuit of transistor 84 and a diode 90 is connected across the emitter-collector circuit for transistor 86. The cathode of diode 88 is connected to the collector while the anode is connected to ground. Likewise, the cathode of diode 90 is connected to the collector while the anode is connected to the ground.

Likewise, line 60 is connected to common bases 100 and 102 of NPN transistors 104 and 106, respectively. A diode 108 is connected across the emitter-collector circuit of transistor 104, and a diode 70 is connected across the emitter-collector circuit of transistor 106. The cathode of diode 108 is connected to the collector while the anode is connected to ground. Likewise, the cathode of diode 110 is connected to the collector while the anode is connected to ground. An appropriate signal on line 60 will switch transistors 104 and 106 into either conduction or non-conduction as desired, to place capacitors 53 and 54 either in or out of the circuit, as desired.

Referring back to FIG. 1, in a receiver 114 of telemetry unit 14, corresponding ends of the outer pick-up coils 26 and 28 are interconnected by a potentiometer 116 and the other ends are connected to a positive DC voltage at point 118. A phase shift detector 120 is connected via line 122 to point 124 in the output to the oscillator coil 24 in order to receive the carrier signal as a reference input. The wiper 126 of potentiometer 116 picks off a signal induced in the pick-up coils 26 and 28, which signal is inputted at point 128 to phase shift detector 120. By comparing the signal at point 124 with the signal at point 128, the phase shift detector 120 produces an output level indicative of the displacement of the phase angle of the received signal at point 128 relative to the carrier signal at point 124. When telemetry unit 14 is in position for transmission, the signal at point 128 will include the reflected signal from the implanted transponder 10 as well as the attenuated carrier.

The phase angle output level of the detector 120 is passed to an acquisition circuit 130 which produces a signal indicative of acquisition when the output level of detector 120 exceeds a threshold value. During reception of data, the output of phase shift detector 120 is fed to a signal processing circuit 132 which reconstructs the data signal being received at point 128.

For additional circuit and parameter details reference is hereby made to U.S. Pat. No. 4,361,153, the disclosure of which is incorporated herein.

In its programming mode, the data signal transmitted via amplifier 22 and middle coil 24 is received by the tank circuit. The tank circuit has matched resistors 140 and 142, and parallel diodes 144, 146 to form a protective clamp for the inputs to comparator 148. The coil signals are coupled into comparator 148 through capacitors 150 and 152, to protect against power line frequencies and their low order harmonics. A resistor 154 is utilized across the comparator inputs to produce a threshold value and to protect against positive offset voltage problems with the comparator.

The output of comparator 148 is connected to the gate of FET switch 156. FET switch 156 serves as an invertor and rectifier to drive the filter 158, which filter comprises resistor 160 and capacitor 162. The filtered signal is fed to a Schmitt trigger 164 which provides the digital output for the logic circuitry.

It can be seen that a system has been provided by which the implanted tank circuit can be tuned to the frequency of the carrier signal that is generated by the telemetry and programming unit. Additional shunt circuits controlled by microprocessor 66 may be used to provide additional tuning selection.

Although illustrative embodiments of the invention have been shown and described, it is to be understood that various modifications and substitutions may be made by those skilled in the art without departing from the novel spirit and scope of the present invention.

What is claimed is:

1. In an implant communication system for use with an external telemetry and programming unit which generates a magnetic carrier signal at a selected frequency, and in which an implanted enclosure carries a tuned coil and a low impedance shunt circuit connected across the tuned coil including a device for modulating the impedance of the shunt circuit in accordance with a data signal to alter the phase and amplitude of a signal reradiated by said tuned coil in the presence of an externally generated magnetic carrier signal at a selected frequency, the improvement comprising:

second shunt circuit means connected across said tuned coil including means for changing the tuning of the tuned coil to enable the tuned frequency to correspond to said selected frequency.

2. In an implant communication system as described in claim 1, said second shunt circuit means comprising a capacitor and a switch; and means for operating said switch.

3. In an implant communication system as described in claim 1, said second shunt circuit means comprising a pair of capacitors and a pair of FETs, with each FET having is source connected to ground, its drain connected to one of the capacitors, and its gate connected to the gate of the other FET; and means coupled to said gates for switching the state of both FETs.

4. In an implant communication system as described in claim 1, said second shunt circuit means comprising a pair of capacitors and a pair of transistors with each transistor having one of its electrodes connected to ground, a second of its electrodes connected to one of said capacitors, and its third electrode connected to the similar electrode of the other transistor; and means coupled to said third electrode and said transistors for switching the state of both transistors.

5. In a tank circuit comprising a coil tuned to a first frequency, the improvement comprising:

shunt circuit means connected across said tuned coil including means for changing the tuning of the tuned coil to enable the tuned frequency to correspond to a selected frequency, said shunt circuit comprising a pair of capacitors and a pair of FETs, with each FET having its source connected to ground and its drain connected to one of the capacitors and its gate connected to the gate of the other FETs; and means coupled to said gates for switching the state of both FETs.

6. A process for communicating data to and from a patient, comprising the steps of:

implanting in the patient an enclosure having a tuned coil mounted therein, said tuned coil being adapted to reradiate a signal in the presence of an externally generated carrier signal;

providing across the tuned coil a variable impedance device whose resistance can be altered in response to a data signal;

providing across the tuned coil a shunt circuit including a capacitor and a switch; and changing the tuning of the tuned coil by operating the switch to enable the tuned frequency to correspond to a selected frequency.

7. A process for communicating data to and from a patient as described in claim 6, said shunt circuit comprising a pair of capacitors and a pair of FETs, with each FET having its source connected to ground, its drain connected to one of the capacitors, and its gate connected to the gate of the other FET; and means coupled to said gates for switching the state of both FETs.

* * * * *